United States Patent

Conley et al.

[11] Patent Number: 5,242,404
[45] Date of Patent: Sep. 7, 1993

[54] ASPIRATION CONTROL SYSTEM

[75] Inventors: Paul G. Conley, St. Charles; Daniel L. Williams, Jr., Florissant; Peter F. Appelbaum, St. Louis, all of Mo.

[73] Assignee: American Cyanamid Company, Stamford, Conn.

[21] Appl. No.: 834,450

[22] Filed: Feb. 12, 1992

[51] Int. Cl.$^5$ .............................................. A61M 31/00
[52] U.S. Cl. ...................................... 604/119; 604/30; 604/35; 604/67
[58] Field of Search ................ 604/22, 28, 30, 35, 604/65, 67, 118, 119, 120, 121

[56] References Cited

U.S. PATENT DOCUMENTS

| | | | |
|---|---|---|---|
| 3,360,185 | 12/1967 | Woolridge | 230/12 |
| 3,599,639 | 8/1971 | Spotz | 604/119 |
| 3,920,014 | 11/1975 | Banko | |
| 4,024,185 | 5/1977 | Wallach | |
| 4,168,707 | 9/1979 | Douvas et al. | |
| 4,180,074 | 12/1979 | Murry et al. | |
| 4,395,258 | 7/1983 | Wang et al. | 604/119 |
| 4,468,219 | 8/1984 | George et al. | 604/66 |
| 4,664,601 | 5/1987 | Uchida et al. | 417/27 |
| 4,670,006 | 6/1987 | Sinnett et al. | 604/26 |
| 4,706,687 | 11/1987 | Rogers | |
| 4,740,202 | 4/1988 | Stacey et al. | 601/19 |
| 4,757,814 | 7/1988 | Wang et al. | |
| 4,759,349 | 7/1988 | Betz et al. | |
| 4,770,187 | 9/1988 | Lash et al. | |
| 4,770,654 | 9/1988 | Rogers et al. | 604/22 |
| 4,790,816 | 12/1988 | Sundblom et al. | 604/31 |
| 4,810,242 | 3/1989 | Sundblom et al. | 604/28 |
| 4,838,281 | 6/1989 | Rogers et al. | |
| 4,898,579 | 2/1990 | Groshong et al. | 604/67 |
| 4,902,276 | 2/1990 | Zakko | 604/28 |
| 4,988,336 | 1/1991 | Kohn | 604/67 |

Primary Examiner—Ralph Lewis
Attorney, Agent, or Firm—Douglas E. Denninger

[57] ABSTRACT

An aspiration control system includes a motor and vacuum pump which are controlled by a system controller, in accordance with input commands to provide a precise, continuously variable vacuum or negative pressure within a vacuum chamber and surgical handpiece. The resulting vacuum is proportional to the control signal sent from the system controller to the motor. A transducer samples the vacuum output and produces a signal fed system controller. The signal is compared with a variable input signal set by a potentiometer or other signal source activated by the input commands so that the transducer signal tracks the voltage source signal. Therefore, the vacuum output of the vacuum pump and motor relates directly and predictably to the input commands. In one embodiment the motor is a brushless DC motor. The system may also include a pinch valve provided on a fluid aspiration conduit communicating between the surgical handpiece and vacuum chamber so that the fluid aspiration at the handpiece may be controlled independently from the negative pressure level created in the vacuum chamber.

20 Claims, 3 Drawing Sheets

ASPIRATION CONTROL SYSTEM

BACKGROUND OF THE INVENTION

The present invention relates to an aspiration control system for microsurgical instruments and in particular to an aspiration control system that is adapted for use in intraocular surgery to control, in accordance with commands received from a surgeon's foot control unit or otherwise selected from a control console, the various aspiration functions normally performed manually by a surgical assistant.

In the field of intraocular or ophthalmic surgery, as well as in many other technical disciplines, there is a great need for an aspiration or suction system in which the vacuum or negative pressure source can be highly controlled. In ophthalmic surgery, for example, many phacoemulsification instruments use suction to aspirate the emulsified tissue away from the operative site or to allow the surgeon to "grab onto" pieces of cut tissue for manipulation within the surgical field. And, in an ophthalmic vitrectomy operation, many cutting instruments draw the tissue into the cutting edges by use of suction. In fact, the tissue removal rate or fluid flow rate is effectively controlled by the suction effect which is related directly to the negative pressure level. Thus, controlling the negative pressure level to a fine degree is highly desirable to provide to the surgeon a concomitant degree of control of the tissue removal process.

However, prior art suction devices are generally deficient in their poor control of the vacuum level or in their reliance on either an outside vacuum source or pressurized air source. Many systems employ a pressure delivery tank in which the vacuum level is controlled by selective connection to a lower pressure source. These types of systems are characteristically underdamped pressure oscillators, in that the negative pressure level often swings wildly about the desired and often changing vacuum level. Also, the large volume of most systems causes a delay in their response, which may lead to poor user control and overshooting of the desired vacuum level.

Many prior art systems use peristaltic pumps or diaphragm pumps to generate the desired vacuum. Examples of such systems are disclosed in U.S. Pat. Nos. 4,180,074; 3,920,014 and 4,168,707. These pump systems are sometimes noisy and are slow to generate the desired vacuum level. Further, it is desirable to have a fast response time for changes in the desired vacuum levels which is difficult to obtain with the use of a peristaltic type pump vacuum system. It is important to realize that such peristaltic pump systems can regulate the fluid flow out of the operative site but cannot control the vacuum level. Such pumps work by pulling the fluid versus controlling the negative pressure level. Further, the working characteristics of a peristaltic pump require use with specific tubings having a known durometer. Over time, the tubing becomes hard thereby changing the operating characteristics of the pump and the reliability of the peristaltic pump system. Furthermore, if a blockage of the aspiration needle of the surgical handpiece occurs, the peristaltic pump keeps trying to pull fluid out of the operative site thereby creating an uncontrolled vacuum rise in the tubing. Upon removal of the blockage, an aspiration surge occurs which can aspirate unintended material out of the operative site possibly causing irreparable damage to the patient's eye.

Various other prior art patents create a vacuum by use of a regulated fluid pressure which is fed through a linear solenoid valve to a venturi-type pressure vacuum converter as is shown in U.S. Pat. Nos. 4,838,281; 4,770,654; 4,810,242 and 4,706,687. The resulting vacuum is proportional to the flow through the solenoid valve and thus to a function of the current through the solenoid. However, in such vacuum systems, the regulated fluid pressure is generated by an outside air supply such as a compressor. In such cases, the compressed air is fed into the microsurgical system under pressure to the air to vacuum converter such as a venturi pump.

This technique for generating a vacuum is wasteful because it requires high rates of air flow to create the vacuum or negative pressure. And, typically the compressor is located externally from the operating area where the surgical procedure is being performed. This would also produce an additional energy waste because the compressor has to work harder to pump the compressed air through the long lengths of tubing to bring the compressed air to the operative site.

Microsurgical devices that depend on an external air pressure source to generate a vacuum are only as reliable as the external air pressure source. Such surgical devices can obviously only operate where such external air pressure sources are available and in good working order. And, while many hospitals in the United States have such external air pressure sources, individual clinics or physicians' offices may not. Further, in many foreign countries low and/or unregulated air pressure sources can disrupt the operation of such microsurgical devices.

It is, therefore, an object of the present invention to have a microsurgical system which is able to generate a controlled vacuum internally to the system in such a way as to operate on electricity only with very little waste.

A further object is to provide a more reliable microsurgical system having a vacuum delivery system that is completely independent of any outside or external air pressure source.

An additional object is to provide a vacuum delivery apparatus which includes precise vacuum control with high response throughout a selected range of vacuum pressure levels by using an electrical motor speed control.

Another object is to provide a reliable motor speed control device to control a vacuum pump based on a closed loop feedback signal from a pressure transducer to precisely control the negative air pressure without any dependency on an external or outside air pressure supply source.

A further object of the present invention is to provide a microsurgical system utilizing a vacuum delivery apparatus having a power consumption which is linearly proportional to the negative pressure required for use by the surgeon during an ophthalmic surgical operation.

And, a still further object of the present invention is to provide a microsurgical system utilizing a vacuum delivery apparatus which can supply a high negative pressure level without a high fluid flow out of the eye or operative site. The fluid flow out of the eye or operative site can be controlled independently of the vacuum pressure level.

SUMMARY OF THE PRESENT INVENTION

The present invention generally comprises a vacuum or negative pressure delivery system which features precise, continuously variable, predictable control of the vacuum delivered. A significant feature is that the variation in vacuum may be adjusted electronically to follow any desirable linear or non-linear relationship to a control signal generated by a system controller. For example, the system may be arranged so that the vacuum level will vary linearly with respect to the position of a control lever, pedal, or the like. The negative vacuum pressure will not fluctuate wildly, and the vacuum at any position of the control lever or pedal is predictable and reproducible. The system may be adapted to surgical suction/evaluation systems and the like, as well as to other technical disciplines.

The system controller provides an electronic control of the entire system and can accomplish this control in an analog or digital, or combination thereof, circuit system. A digital circuit system would utilize a microprocessor to provide the necessary control signal to a motor controller and motor. An analog circuit system would utilize a differential amplifier of a proportional, integral and differential (PID) type to provide a control signal to a motor controller and motor. Depending on the type of system controller utilized, it may be possible for the signal controller to operate the motor directly without the use of a separate motor controller.

The system further uses a rotary type vacuum pump which is controlled by a precisely controlled electrical motor. In one embodiment, the motor is a brushless direct current (DC) motor which is controlled by a DC motor controller. In an alternate embodiment, the motor is a three phase motor which is controlled by a three phase inverter powered by a single phase 115 volt electrical power line.

In the preferred embodiment an alternating current (AC) line voltage is supplied to a power supply. The power supply changes the voltage and current from a 115 volt AC to a 24 volt DC output. This output is then supplied to a DC motor controller which, in turn, determines and regulates the rotational speed and output the brushless DC motor and of the vacuum pump.

The vacuum level of the pump is sampled by a pressure transducer which sends a feedback signal to a summing junction and differential amplifier positioned in the system controller. An electrical reference signal corresponding to the input level desired by the operator as controlled by a foot pedal is also fed to the system controller. The two signals are compared by the system controller which then feeds a control signal to the DC motor controller to change the speed of the brushless DC motor and thus the aspiration level as necessary. A linear relationship between the signal from the transducer and the aspiration level provides a source of comparison with the user command signal.

The level of aspiration produced in the surgical handpiece is thus controlled by the rotational speed of the vacuum pump which in turn is controlled by the rotational speed of the DC motor. The rotational speed of the motor is determined by the control voltage input to the DC motor controller from the motor controller. A vacuum level control valve is also supplied to help provide a pressure drop and at the same time supply a predetermined flow of air to the vacuum pump.

A pinch valve can also be supplied on the fluid return line from the surgical handpiece to allow the amount of fluid being drawn away from the operative site to be controlled without increasing or decreasing the vacuum level created by the vacuum pump. A shut-off valve may also be included in the vacuum line to allow immediate cessation of the aspiration if necessary.

Other objects features and advantages of the invention will be readily apparent from the following description of certain preferred embodiments thereof taken in conjunction with the accompanying drawings, although variations and modifications may be effected without departing from the spirit and scope of the novel concepts of the disclosure.

DETAILED DESCRIPTION OF THE INVENTION

The present invention generally comprises an aspiration control system which features exacting control of a vacuum which is generated and delivered to a surgical handpiece. The aspiration control system of the present invention is used as an integral part of a microsurgical system for support of eye surgeons in performing eye surgery. The microsurgical system supplies various functions needed for eye surgery and allows the surgeon to control critical parameters of each function. To implement and control the various functions, a central processing unit or system controller, reads a plurality of switches and sensors to control a pneumatic system which drives surgical scissors and/or supplies a liquid infusion bottle to provide infusion fluid to the surgical handpiece. The system controller also reads certain controls and converts signals from them into on/off control signals to control an ultrasonic fragmentation device in a surgical handpiece for removal of cataracts or perform various other surgical operations. And, in accordance with the present invention, such a control unit also controls the aspiration control system used to aspirate cut or fragmented tissue and fluids which accumulate in the operating area during vitrectomies or cataract removal operations.

Figure 1:
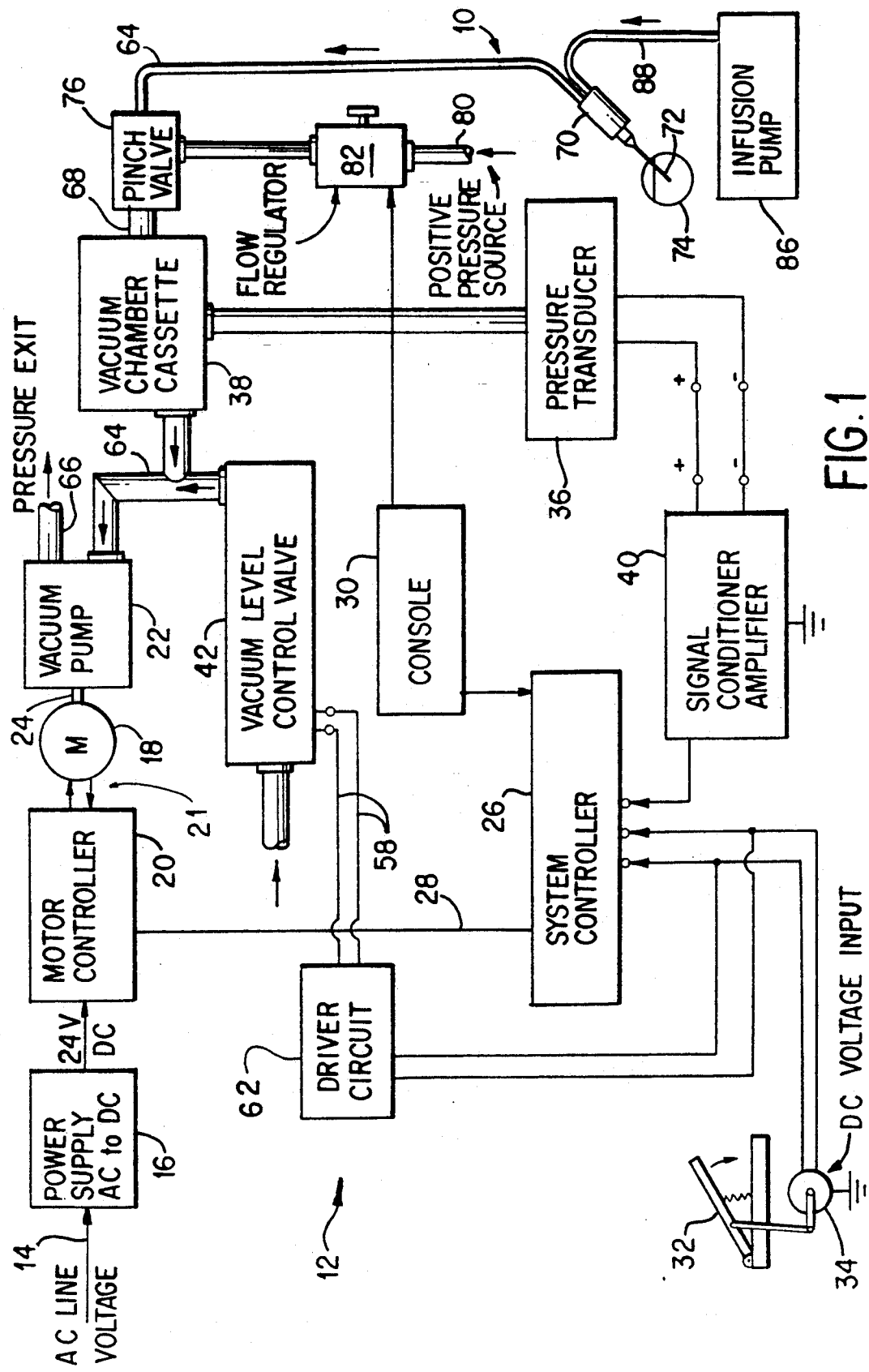
FIG. 1 is a functional block diagram of the aspiration control system of the present invention.

With reference to FIG. 1, the microsurgical system 10 includes an aspiration delivery system 12. In the preferred embodiment, an alternating current line voltage 14 is provided to power supply 16. The power supply 16 changes the voltage from 115 volt (v) AC as supplied by the AC line voltage 14 to a 24 volt DC output to be supplied to a brushless DC motor 18 via a DC motor controller 20. The motor controller 20 includes a PID type controller to precisely regulate the speed of the brushless DC motor 18. A feedback loop 21 from the DC motor 18 to the motor controller 20 is provided to assist in the control of the DC motor's rotational speed.

One such brushless DC motor is manufactured by Fasco Industries, Inc. of St. Louis, Missouri. One such motor controller 20 is manufactured by Dart Controls, Inc. of Zionsville, Indiana. However, DC motor 18 and motor controller 20 could be obtained from various other sources as long as such motor 18 and motor controller 20 would operate within the parameters of the overall system. It may also be possible to integrate the separate motor controller 20 into the system controller 26 such that a separate motor controller would be unnecessary.

The system controller 26 supplies a low level control signal 28 to the motor controller 20 to adjust the speed of the motor 18. The motor 18 is connected to a rotary vane vacuum pump 22 via shaft 24. Therefore, the various aspiration levels are controlled by the rotational speed of the vacuum pump 22 which is controlled by the motor controller 20 and system controller 26.

One such vacuum pump 22 as disclosed above is manufactured by Gast Manufacturing Company of Ann Arbor, Michigan. However, vacuum pump 22 could also be of a different type pump such as either a diaphragm pump, or an impeller pump, or a liquid ring impeller pump.

A user input console 30 is used to input the vacuum levels and aspiration rise time, which is the amount of time it takes the system to provide the selected vacuum from a 300 vacuum style. The console 30 feeds these commands into the system controller 26 for processing. The system controller 26 is also fed a reference signal generated by an analog variable voltage device, such as a potentiometer or by a digital signal encoder 34. The potentiometer 34 is activated by a mechanical control device, such as a foot pedal 32 having a continuously variable range of angular position settings which are directly related to the potentiometer setting.

Full pedal deflection of the foot pedal 32 will give a corresponding full aspiration level as selected by the operator at the console 30. Zero pedal deflection of said foot pedal 32 will correspond to a zero aspiration level. The aspiration level is proportional to the pedal deflection. For example, if 300 mm Hg is selected by the user at the console 30 and the foot pedal 32 is depressed one-half full pedal deflection, the aspiration level achieved will be 150 mm Hg.

It may be appreciated that other reference voltage sources may be employed, such as a system controller system in which the pedal system of the foot pedal 32 is read by a linear shaft position encoder.

A pressure transducer 36 measures the vacuum level produced in a vacuum chamber cassette 38 by the vacuum pump 22. The transducer 36 generates a signal which is fed to the system controller 26 through a signal conditioner/amplifier 40. The signal conditioner/amplifier 40 conditions the signal from the pressure transducer 36 to a level for processing by the system controller 26. The system controller 26 will compare and track the signal produced by vacuum levels sensed in the vacuum chamber cassette 38 to the input command received from the console 30 and the foot pedal deflection from foot pedal 32. The system controller 26 then sends a control signal to DC motor controller 20 to adjust the motor speed of the DC brushless motor to where the measured difference of desired vacuum and actual vacuum is zero. The vacuum chamber cassette 38 is also utilized to collect the aspirated fluid and tissue from the surgical site through a handpiece 70 as discussed below.

Figure 2A:
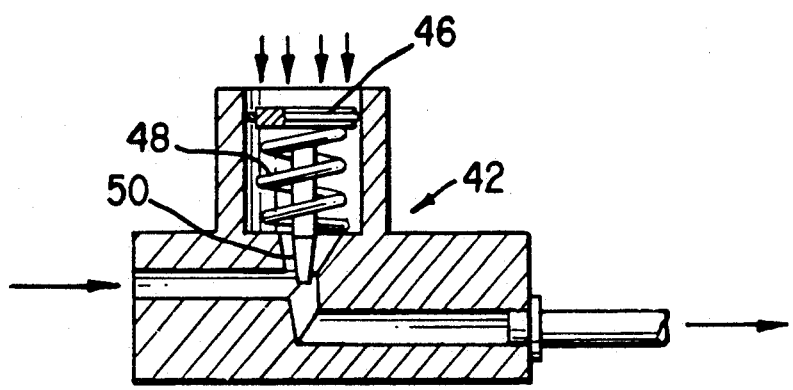
FIG. 2a is a cross-sectional elevation of a mechanically operated vacuum control valve according to one embodiment of the present invention.

A vacuum level control valve 42 is utilized to provide a pre-determined air flow into the vacuum pump 22. The vacuum level control valve 42 has a pre-determined orifice size which can be controlled by atmospheric pressure or the system controller to assist in the change of the vacuum level. As shown in FIG. 2a, the vacuum level control valve 42 can be controlled mechanically by a diaphragm 46 and spring 48 acting on the needle pin 50. In this embodiment, as the vacuum level changes, a corresponding change in pressure across the diaphragm 46 causes the needle pin 50 to move to increase or decrease the orifice opening accordingly to assist in achieving a certain vacuum level.

Figure 2B:
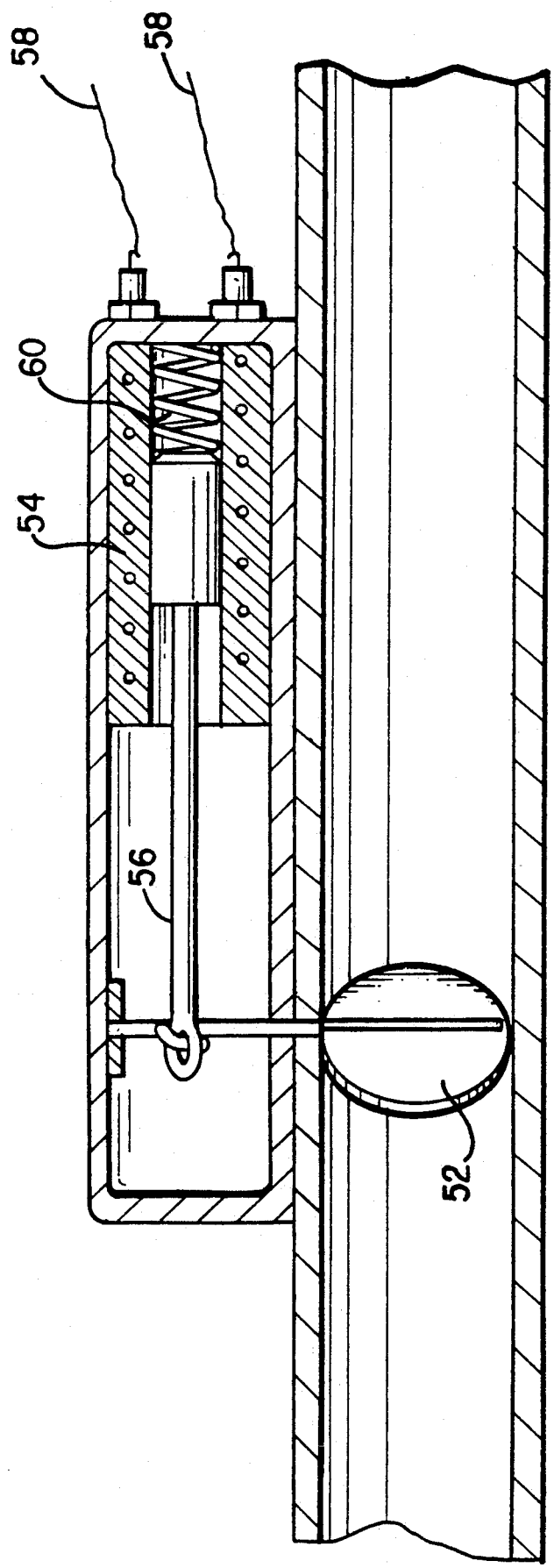
FIG. 2b is a cross-sectional elevation of an electrically operated vacuum control valve according to another embodiment of the present invention.

FIG. 2b illustrates a second embodiment of the control valve 42 having a controllable disc member 52 which is controlled by movement of a mechanical arm 56 within coil 54 in response to an electrical signal received from the system controller 26. A return spring 60 provides resistance to movement of control arm 56, and when no current is supplied to coil 54, returns the disc member 52 to its original position within control valve 42. The control valve 42 shown in FIG. 2b and FIG. 1 is controlled by running an open loop signal from the system controller 26 through a driver circuit 62 to the electrically operated control valve 42 such that a signal from the foot pedal controller 32 via potentiometer or digital encoder 34 will act to open and close the disc member 52 of control valve 42. The driver circuit 62 acts to condition the electrical signal from foot pedal 32 to the proper voltage level required by the control valve 42. As the foot pedal deflection increases, an electric signal over wires 58 will cause the mechanical arm 56 to move against the force of the return spring 60 until the force induced by the coil 54 is equal to the restrictive force of the spring to move disc member 52 to change the orifice size within the control valve 42 by a predetermined amount to assist the operator in achieving various vacuum levels.

Control valve 42 allows the system to operate in the preferred speed range of the vacuum pump 22 and DC motor 18. For example, at a 3/16" diameter orifice size of valve 42, the vacuum pump will operate at its minimum specified speed (i.e. 800 rpm) without creating a vacuum or negative pressure in vacuum cassette. This is desirable so that upon actuation of the microsurgical system, no vacuum level will be generated in the vacuum cassette by the vacuum pump. On the other hand, to achieve a high vacuum level in the vacuum cassette, such as 650 mn Hg, the system will close down the orifice and increase the pump speed so as to obtain a high vacuum level (i.e. 650 mm Hg). The variable orifice size allows the system to create the higher vacuum levels without increasing the speed of the DC motor or vacuum pump to a level that would be unacceptable from a noise point of view (55 dB).

In an alternate embodiment, the control valve 42 can be operated in a closed loop circuit (not shown) in conjunction with the motor 18 and pump 22. This would enable the system controller 26 to minimize the electrical power consumption of the motor 18 and vacuum level control valve 42 to achieve the desired vacuum level within the vacuum chamber cassette 38.

Referring to FIG. 1, it is seen that through operation of the vacuum pump 22 that a partial vacuum or negative pressure is created in the vacuum chamber cassette 38 through conduit 64. The vacuum pump 22 will exhaust air through conduit 66 either internally or externally to the cabinet (not shown) which houses all of the components of the microsurgical system. The vacuum chamber cassette 38 has another conduit 68 leading to a surgical handpiece 70 having a needle member 72 providing both liquid infusion and aspiration conduits therein for performing the various surgical procedures on an eye 74 required during a vitrectomy or cataract removal operation.

Figure 3:
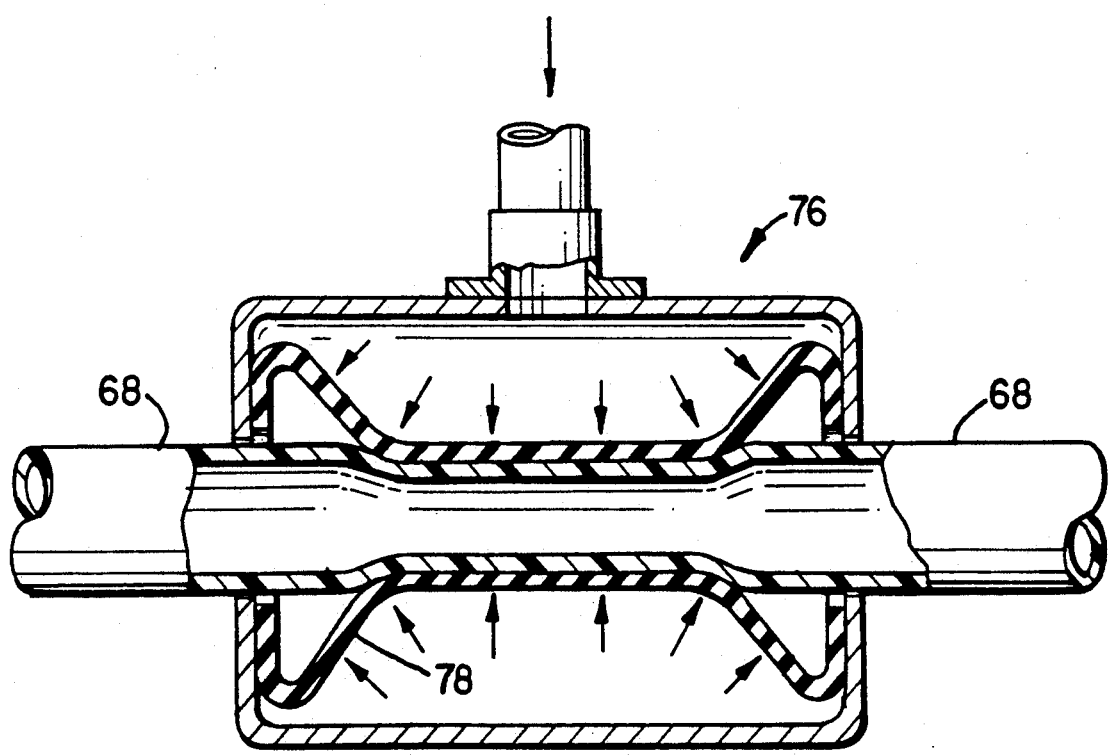
FIG. 3 is a cross-sectional elevation of the pinch valve according to the preferred embodiment of the present invention.

Due to the negative pressure created in the vacuum chamber cassette 38, the surgical handpiece will aspirate fluid out of the eye through conduit 68 during the various surgical operations. It is often times desirable for the operator to decrease the fluid being aspirated by the surgical handpiece without decreasing the vacuum level produced by vacuum pump 22. Referring to FIGS. 1 and 3, a pinch valve 76 is provided on conduit 68. Pinch valve 76 includes a diaphragm 78 which in response to a positive pressure source 80 restricts the effective area of the conduit 68 to reduce the flow of fluid through the conduit. A flow regulator 82 regulates the amount of pressurized air provided to the pinch valve 76 in response to an input command from the system controller 26. The greater the amount of pressurized air provided in the pinch valve, the more the diaphragm expands further restricting the effective area of the conduit 68 and, thereby, further limiting the flow of fluid through the conduit.

The benefit of such a pinch valve is that the operator can control the flow of fluid out of the eye independently of the level of vacuum or negative pressure created by the vacuum pump. This allows the operator to have a low flow rate of fluid exiting the eye while at the same time having a relatively large vacuum level available for use at the tip of the surgical handpiece for manipulating pieces of tissue within the operative site. In an alternate embodiment, it would be possible to control the flow regulator 82 via the foot pedal 32 so that the operator could change the aspirated fluid flow rate at the surgical handpiece without using his hands or relying on assistants to manipulate the controls at the console 30.

In one embodiment of the present invention, the system controller 26 would consist of a PID type differential amplifier with a summing junction that would receive the input signals from the transducer feedback signal and input commands from the console and foot pedal. The system controller thereafter would provide a control signal to the DC motor controller to precisely control the speed of the brushless DC motor. In another embodiment the system controller 26 would consist of a microprocessor to provide the necessary control signal to the motor controller or DC motor.

In an alternate embodiment, the motor 18 would be a three phase 115 volt electrical motor. The motor controller 20 would be a three phase inverter powered by a single phase 115 volt electrical power line. The three phase inverter would control the speed and power of the three phase motor which in turn would regulate the rotational speed and output of the vacuum pump 22. This embodiment would operate in a similar fashion to that discussed above. The vacuum level of the pump 22 is sampled and fed to a pressure transducer 36 which sends a feed back signal to a signal conditioner/amplifier 40 for transmission to the system controller 26. An electrical reference signal corresponding to the input vacuum level desired by the operator as controlled by the foot pedal controller 32 is also fed to the system controller 26. The two signals are compared in the system controller and a control signal is sent to the three phase inverter motor control 20 to change the speed of the motor 20 and thus the aspiration level as necessary. A linear relationship between the signal from the transducer 36 and the aspiration level provides a source of comparison with the operator's command signal.

The level of aspiration produced in the surgical handpiece is thus controlled by the rotational speed of the vacuum pump 22 which in turn is controlled by the frequency of the three phase voltage supplied to the motor 18 by the inverter. A vacuum level control valve 42, pinch valve 76 and flow regulator 82 could all be provided as discussed above.

The microsurgical system 10 would further include an infusion pump system 86 for providing the surgical handpiece 70 with fluid irrigation through conduit 88 to assist the operator in the various ophthalmic surgical procedures required in vitrectomies or cataract removal operations.

Although the invention has been described in terms of the embodiments described above, it will be apparent to those skilled in the art that numerous modifications can be made such as the type of vacuum pump or system controller utilized to perform the basic functions of the aspiration control system. All such modifications, if they fall within the spirit of the invention are intended to be covered by the claims set out below.

What is claimed is:

1. A surgical aspiration system for aspirating fluid and cut tissue from an operative site through a surgical handpiece into a vacuum chamber, the system comprising:

a vacuum pump for creating a negative pressure within the vacuum chamber, including conduit means adapted for connection with the vacuum chamber;

a motor mechanically connectable to the vacuum pump for operating the vacuum pump;

transducer means, adapted for placement in pressure communication with the vacuum chamber, for sensing the vacuum within the vacuum chamber and for generating a first signal in response thereto;

input means for selecting an appropriate vacuum level for aspirating fluid and cut tissue and for generating a second signal which corresponds to the vacuum level;

variable reference voltage source means for generating a selectively variable reference voltage; and controller means, connected to said transducer means, said input means, and said variable reference voltage source means, for comparing said first and second signals and the variable reference voltage and generating an output signal representing the difference as determined by the controller means between the first signal and the second signal as modified by the variable reference voltage, said output signal being connected to drive said motor and vacuum pump to control the vacuum level within said vacuum chamber.

2. The surgical aspiration system of claim 1, wherein said reference voltage source means includes a control device having a movable control element which varies said reference voltage in accordance with the position thereof.

3. The surgical aspiration system of claim 2, wherein said controller means includes means for adjusting the overall response of said system so that incremental change in the position of said control element bears a predetermined and reproducible incremental change in the vacuum level output of said vacuum pump.

4. The surgical aspiration system of claim 3, wherein said overall response is a linear relationship between change in position of said control element and change in the level of vacuum output of said vacuum pump.

5. The surgical aspiration system of claim 4, wherein said control device comprises a foot pedal having a continuously variable range of angular position settings and said control element comprises a potentiometer having a corresponding number of variable position settings directly related to the foot pedal settings.

6. The surgical aspiration system of claim 5 wherein said motor is a brushless DC motor.

7. The surgical aspiration system of claim 6, wherein said motor further includes a motor controller having a PID type function receiving the control signal from the controller means and sending a second control signal to the motor to precisely regulate the rotational speed and output of said motor and vacuum pump.

8. The surgical aspiration system of claim 5 further comprising a vacuum level control valve, responsive to the foot pedal, having a known variable orifice diameter to provide a pre-determined air flow into the vacuum pump to assist the motor and vacuum pump in providing a precisely controlled vacuum at an efficient motor speed, and including means for changing the orifice diameter as the foot pedal is depressed.

9. The surgical aspiration system of claim 8 further comprising a pinch valve means positionable on a fluid conduit extending from the surgical handpiece to the vacuum chamber to separately constrict the flow of fluid being aspirated by the surgical handpiece into the vacuum chamber.

10. The surgical aspiration system of claim 9 wherein the pinch valve means comprises:
a valve having a diaphragm for surrounding said fluid conduit; and
a flow regulator to regulate the amount of pressurized air provided from a positive pressure source to the valve diaphragm such that the fluid flow being aspirated through the surgical handpiece can be controlled independently from the vacuum level in the vacuum chamber.

11. A surgical aspiration system for aspirating fluid and cut tissue from an operative site through a surgical handpiece into a vacuum chamber, the system comprising:
a vacuum pump for creating a negative pressure within the vacuum chamber, including conduit means adapted for connection with the vacuum chamber;
a motor mechanically connectable to said vacuum pump for operating said vacuum pump;
transducer means, adapted for placement in pressure communication with the vacuum chamber, for sensing the vacuum within the vacuum chamber and for generating a first signal in response thereto;
input means for selecting an appropriate vacuum level for aspirating and cutting tissue and for generating a second signal which corresponds to the vacuum level;
a foot pedal having a continuously variable range of angular position settings which correspond to an analog voltage signal via potentiometer or a digital signal via an encoder which sends a third signal to controller means for regulating a control signal being sent to said motor; and
controller means, connected to said transducer means, said input means, and said foot pedal, for comparing the first and second signals and generating the control signal to regulate the rotational speed and output of said motor such that the aspiration level within the vacuum chamber and surgical handpiece can be precisely controlled by said controller means, wherein said controller means comprises a feedback circuit for comparing the first, second and third signals from said transducer means, said input means and said foot pedal, respectively, and generating the control signal to cause the surgical aspiration system to generally follow the second signal as modified by the third signal.

12. The surgical aspiration system of claim 11 wherein said motor is a brushless DC motor, and said feedback circuit changes the level of the control signal as the third signal decreases to reduce the negative pressure within the vacuum chamber.

13. A surgical aspiration system of claim 11 wherein the system controller is of a proportional, integral and differential (PID) type and utilizes an analog circuit system.

14. A surgical aspiration system for aspirating fluid and cut tissue from an operative site through a surgical handpiece into a vacuum chamber, the system comprising:
a vacuum pump for creating a negative pressure within the vacuum chamber, including conduit means adapted for connection with the vacuum chamber;
a motor mechanically connectable to said vacuum pump for operating said vacuum pump;
transducer means, adapted for placement in pressure communication with the vacuum chamber, for sensing the vacuum within the vacuum chamber and for generating a first signal in response thereto;
input means for selecting an appropriate vacuum level for aspirating and cutting tissue and for generating a second signal which corresponds to the vacuum level;
a foot pedal having a continuously variable range of angular position settings which correspond to an analog voltage signal via potentiometer or a digital signal via an encoder which sends a third signal to controller means for regulating a control signal being sent to said motor; and
controller means, connected to said transducer means, said input means, and said foot pedal, for comparing the first and second signals and generating a control signal to regulate the rotational speed and output of said motor such that the aspiration level within the vacuum chamber and the surgical handpiece can be precisely controlled by said controller means, wherein said controller means comprises a summing junction which consists of a differential amplifier to which is input the first signal from said transducer means representing current vacuum level and the second signal representing a reference signal from said input means as modified by the third signal.

15. The surgical aspiration system of claim 14 wherein said motor is a brushless DC motor, and said summing junction changes the level of the control signal as the third signal decreases to reduce the negative pressure within the vacuum chamber.

16. A surgical aspiration system for aspirating fluid and cut tissue from an operative site through a surgical handpiece into a vacuum chamber, the system comprising:

a vacuum pump for creating a negative pressure within the vacuum chamber, including conduit means adapted for connection with the vacuum chamber;

a brushless DC motor mechanically connectable to said vacuum pump for operating said vacuum pump;

said motor further including a motor controller having a PID type controller receiving a control signal from controller means and sending a second control signal to said motor to precisely regulate the rotational speed and output of said motor and said vacuum pump, and said motor controller receiving a feedback signal from said motor to precisely control the speed of said motor;

transducer means, adapted for placement in pressure communication with the vacuum chamber, for sensing the vacuum within the vacuum chamber and for generating a first signal in response thereto;

input means for selecting an appropriate vacuum level for aspirating and cutting tissue and for generating a second signal which corresponds to the vacuum level;

controller means, connected to said transducer means and said input means, for comparing the first and second signals and generating the control signal to regulate the rotational speed and output of said motor such that the aspiration level within the vacuum chamber and the surgical handpiece can be precisely controlled by said controller means.

17. A negative pressure delivery and control system for creating a negative pressure within a vacuum chamber wherein the chamber is in communication through a fluid conduit with a surgical handpiece, comprising:

a vacuum pump for creating the negative pressure within the vacuum chamber including conduit means adapted for connection with the vacuum chamber;

a motor mechanically connectable to said vacuum pump for operating said vacuum pump;

transducer means, adapted for placement in pressure communication with the vacuum chamber, for sensing the negative pressure level within the vacuum chamber and for generating a first signal in response thereto;

input means for selecting an appropriate negative pressure level for aspirating fluid through the surgical handpiece and for generating a second signal which corresponds to said level;

a variable reference voltage source for generating a selectively variable reference voltage;

controller means, connected to said transducer means, said input means, and said variable reference voltage source, for comparing the first and second signals and generating a control signal to regulate the rotational speed and output of said motor such that the negative pressure level can be precisely controlled by said controller means, wherein said controller means further compares the first and second signals and the variable reference voltage and generates the control signal representing the difference as determined by said controller means between the first signal and the second signal as modified by the variable reference voltage; and pinch valve means adapted for placement on the fluid conduit to operatively restrict the flow of fluid being aspirated by the surgical handpiece such that the flow of fluid can be independently controlled from the negative pressure level created by said motor and said vacuum pump.

18. The negative pressure delivery and control system of claim 17 wherein said reference voltage source means includes a control device having a movable control element which varies said reference voltage in accordance with the position thereof.

19. The negative pressure delivery and control system of claim 18, wherein said motor is a brushless DC motor.

20. The negative pressure delivery and control system of claim 18, wherein said motor is a three phase 115 volt electric motor having a three phase inverter powered as a single phase 115 volt electrified power input and receiving the control signal from said controller means to regulate the rotational speed and output of said motor.

* * * * *